United States Patent [19]
Boen et al.

[11] Patent Number: 5,429,768
[45] Date of Patent: Jul. 4, 1995

[54] GRIGNARD REACTION INTERMEDIATES AS BLEACH CATALYSTS

[75] Inventors: Laurence Boen, Wayne, N.J.; Stephen A. Madison, New City, N.Y.

[73] Assignee: Lever Brothers Company, Division of Conopco, Inc., New York, N.Y.

[21] Appl. No.: 156,349

[22] Filed: Nov. 22, 1993

[51] Int. Cl.⁶ .................... C09K 3/00; C11D 3/395; D06L 3/00; C07D 275/04
[52] U.S. Cl. .................... 252/186.39; 252/186.38; 252/186.42; 252/186.43; 252/95; 8/110; 8/111; 548/165; 548/209
[58] Field of Search ............ 252/186.38, 186.39; 548/165, 209

[56] References Cited
U.S. PATENT DOCUMENTS
4,412,934  11/1983  Chung et al. .................... 252/186.38

OTHER PUBLICATIONS

J.C.S. Chem. Comm. 1977, pp. 25–26.
J. Amer. Chem. Soc., 1980, 102, pp. 2,000–2,005.
J. Org. Chem. 1988, 53, pp. 2,087–2,091.
J. Org. Chem. 1988, 53, pp. 5,004–5,007.
CA 82:156163, "Synthesis of 3-Alkyl(or Aryl-)1-,2-Benzothiazole 1,1-Dioxides and Related Compounds." by Abramovitch et al., Univ. of Alabama 1974.

*Primary Examiner*—Gary Geist
*Assistant Examiner*—Joseph D. Anthony
*Attorney, Agent, or Firm*—Milton L. Honig

[57] ABSTRACT

Novel bleach catalysts, a method for bleaching substrates using these catalysts and bleach compositions containing the catalysts are reported. These catalysts are magnesium salts of sulfonimines. Substrates such as fabrics and dishware may be bleached in an aqueous solution containing the magnesium sulfonimine salts and a peroxygen compound.

20 Claims, No Drawings

GRIGNARD REACTION INTERMEDIATES AS BLEACH CATALYSTS

BACKGROUND OF THE INVENTION

1. Field of the Invention

The invention relates to novel bleach catalysts, compositions containing same and the method for using these catalysts in detergent compositions, especially for cleaning fabrics and dishes.

2. The Related Art

Many household and personal care products are formulated with an active oxygen-releasing material to effect removal of stain and soil. Oxygen-releasing materials have an important limitation; their activity is extremely temperature dependent. Temperatures in excess of 60° C. are normally required to achieve any bleach effectiveness in an aqueous wash system. Especially for cleaning fabrics, high temperature operation is both economically and practically disadvantageous.

The art has partially solved the aforementioned problem through the use of activators. These activators, also known as bleach precursors, often appear in the form of carboxylic acid esters. In an aqueous liquor, anions of hydrogen peroxide react with the ester to generate the corresponding peroxyacid which oxidizes the stained substrate. Commercial application of this technology is found in certain fabric bleaching detergent powders incorporating sodium nonanoyloxybenzene sulfonate. This activator is typical of a class that features a phenol sulfonate leaving group; see U.S. Pat. No. 4,412,934 (Chung et al).

While carboxylic acid ester activators and the like are often effective, they are not catalytic. Once the ester has been perhydrolyzed, it can no longer be recycled. Accordingly, relatively large amounts of activator are necessary. Amounts as high as 8% may be necessary in a detergent formulation for bleaching fabrics. Cost for these relatively expensive activators is of major concern at such levels.

Outside the context of consumer products, there have been reports of catalytic oxidizing agents. F. A. Davis and coworkers, in a series of articles, reported preparation of a new class of stable oxidizing agents, namely 2-arenesulfonyl-3-aryloxaziridines. See Davis, Nadir and Gluger, J. C. S. Chem. Comm. 1977, 25; Davis, Lamendola Jr., Nadir, Kluger, Sederjarn, Panunto, Billmers, Jenkins Jr., Turchi, Watson, Chen and Kimura, J. Amer. Chem. Soc. 1980, 102, 2000; and Davis, Chattopadhay, Towson, Lal and Reedy, J. Org. Chem. 1988, 53, 2087. These oxaziridines were prepared by peracid or monopersulfate oxidation of a corresponding sulfonimine under alkaline conditions. In late 1988, Davis published a paper entitled "Selective Catalytic Oxidation of Sulfides to Sulfoxides Using N-sulfonyloxaziridines", J. Org. Chem, 1988, 53, 5004. Therein described is a system where sulfonimine reacts with monopersulfate to generate an in situ oxaziridine in a toluene-water biphasic mixture. Oxaziridine then coverts the sulfide to a sulfoxide and generates starting sulfonimine, thereby rendering the process catalytic in nature.

Sulfonimine chemistry has moved beyond the area of a mere synthetic tool. Recently, suifonimines have been recognized as useful for removing stains in consumer applications such as in the cleaning of fabrics. U.S. Pat. No. 5,041,232 (Batal et al) reports the bleaching activity of sulfonimines such as SULF-11 as effective at bleaching a variety of stains. During investigation of synthetic mutes to SULF-11, the present Applicants discovered certain reaction intermediates which by themselves exhibited catalytic bleaching activity.

Accordingly, it is an object of the present invention to provide novel bleach catalysts and detergent compositions containing such catalysts that operate over a wide temperature range including that of under 60° C.

It is another object of the present invention to provide novel bleach catalysts which are effective at relatively low concentrations thereby achieving a cost-effective stain removal system.

It is a further object of the present invention to provide a method for bleaching stained substrates such as clothes, household hard surfaces including sinks, toilets and the like, and even dentures.

Other objects of the present invention will become more readily apparent through the following summary, detailed description and examples.

SUMMARY OF THE INVENTION

A bleaching composition is provided including:
(i) from about 1 to about 60% by weight of a peroxygen compound; and
(ii) from about 0.05 to about 10% of an oxygen transfer agent whose structure is:

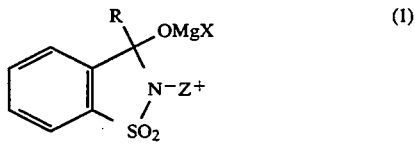

which is solvated with an ether or unsolvated, wherein:
R is a $C_1$–$C_{20}$ alkyl or aryl radical;
$Z^+$ is a metallic cation; and
X is a halide.

Additionally, there is provided a method for bleaching a stained substrate involving the step of applying to the stained substrate an aqueous solution of a peroxygen compound and an oxygen transfer agent whose structure is (1), with radical groups as defined above and being solvated or unsolvated, the mole ratio of peroxygen compound to oxygen transfer agent being from about 250:1 to about 1:2. Certain novel compounds are also provided having structure (1) with radical groups as defined above, with the proviso that $Z^+$ is other than magnesium.

DETAILED DESCRIPTION

It has been found that certain types of magnesium sulfonimine salts can operate as catalysts on peroxygen compounds to transfer active oxygen to stains. Consumer and industrial articles can effectively be bleached to remove stains present on such articles. The magnesium sulfonimine salts have the structure (1):

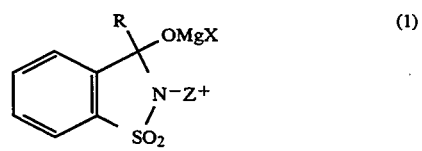

which is solvated with an ether or unsolvated, wherein:

R is a $C_1$–$C_{20}$ alkyl or aryl radical;

$Z^+$ is a metallic cation; and

X is a halide.

Particulary preferred as the R group are methyl, ethyl, propyl, butyl, octyl and phenyl radials. Most preferred as the $Z^+$ are alkalimetal and alkaline earth metal cations. Examples include sodium, potassium, calcium, barium and magnesium cations. Novel compounds are found among the mixed metal salts, especially where $Z^+$ is either sodium or potassium cation. Group X normally is a halide such as chloride or bromide.

Synthetic routes to structure (1) are reported in a copending application (Attorney Docket No. 93-R024-EDG), the disclosure being incorporated herein by reference.

Structure (1) may be solvated with one or more moles of an ether per mole of saccharin. The preferred mole ratio ranges from 1:3 to 1:1 of saccharin to ether. Illustrative ethers are tetrahydrofuran (THF) and diethyl ether, the THF being preferred.

The foregoing oxygen transfer agents may be incorporated into detergent bleach compositions along with a further essential component which is a peroxygen compound capable of yielding peroxide anion in an aqueous solution.

Amounts of oxygen transfer agent suitable for the present invention may range from about 0.05 to about 10%, preferably from about 0.2 to 5%, optimally between about 0.5% and 1.5% by weight of the composition.

The peroxygen compound may be present from about 1 to 60%, preferably from about 1.5 to 25%, optimally from about 2 to 10% by weight.

The molar ratio of peroxide anion (or a peroxygen compound generating the equivalent amount of peroxide anion) to oxygen transfer agent will range from about 250:1 to 1:2, preferably about 100:1 to 1:1, optimally between about 25:1 to 2:1.

Peroxide anion sources are well-known in the art. They include the alkalimetal peroxides, organic peroxides such as urea peroxide, and inorganic persalts, such as the alkalimetal perborates, percarbonates, perphosphates, persilicates and persulfates. Mixtures of two or more such compounds may also be suitable. Particularly preferred are sodium perborate tetrahydrate and, especially, sodium perborate monohydrate. Sodium perborate monohydrate is preferred because it has excellent storage stability while also dissolving very quickly in aqueous solutions.

Alkylhydroperoxides are another suitable class of peroxygen compounds. Examples of these materials include cumene hydroperoxide and t-butyl hydroperoxide.

Organic peroxyacids may also be suitable as the peroxygen compound. Such materials have a general formula:

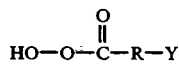

wherein

R is an alkylene or substituted alkylene group containing from 1 to about 22 carbon atoms or a phenylene or substituted phenylene group, and Y is hydrogen, halogen, alkyl, aryl or

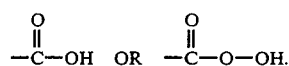

The organic peroxyacids usable in the present invention can contain either one or two peroxy groups and can be either aliphatic or aromatic.

When the organic peroxyacid is aliphatic, the unsubstituted acid has the general formula:

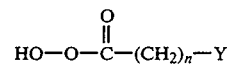

where

Y can be, for example, H, $CH_3$, $CH_2Cl$, COOH, or COOOH; and n is an integer from 1 to 20.

When the organic peroxy acid is aromatic, the unsubstituted acid has the general formula:

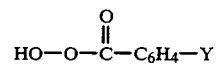

wherein

Y is hydrogen, alkyl, alkylhalogen, halogen or COOH or COOOH.

Typical monoperoxy acids useful herein include alkyl peroxyacids and aryl peroxyacids such as:

(i) peroxybenzoic acid and ring-substituted peroxybenzoic acid, e.g. peroxy-α-naphthoic acid;

(ii) aliphatic, substituted aliphatic and arylalkyl monoperoxy acids, e.g. peroxylauric acid, peroxystearic acid, and N,N-phthaloylaminoperoxycaproic acid;

(iii) amidoperoxyacids, e.g. monononylamide of either peroxysuccinic acid (NAPSA) or of peroxyadipic acid (NAPAA).

Typical diperoxy acids useful herein include alkyl diperoxyacids and aryldiperoxy acids, such as:

(iii) 1,12-diperoxydodecanedioic acid;

(iv) 1,9-diperoxyazelaic acid;

(v) diperoxybrassylic acid; diperoxysebacic acid and diperoxyisophthalic acid;

(vi) 2-decyldiperoxybutane-1,4-dioic acid;

(vii) 4,4'-sulfonylbisperoxybenzoic acid.

Bleach systems of the present invention may be employed for a wide variety of purposes, but are expecially useful in the cleaning of laundry. When intended for such purpose, the peroxygen compound and oxygen transfer agent of the present invention will usually also be combined with surface-active materials, detergency builders and other known ingredients of laundry detergent formulations.

The surface-active material may be naturally derived, such as soap or a synthetic material selected from anionic, nonionic, amphoteric, zwitterionic, and cationic actives and mixtures thereof. Many suitable actives are commercially available and are fully described in the literature, for example in "Surface Active Agents and Detergents", Volumes I and II, by Schwartz, Perry and Berch. The total level of the surface-active material may range from about 0.5 to about 50% by weight, preferably being from about 1% to about 40% by weight of the composition, most preferably 4 to 25%.

Synthetic anionic surface-actives are usually water-soluble alkali metal salts of organic sulfates and sulfonates having alkyl radicals containing from about 8 to about 22 carbon atoms.

Examples of suitable synthetic anionic detergent compounds are sodium and ammonium alkyl sulfates, especially those obtained by sulfating higher ($C_8$–$C_{18}$) alcohols produced for example from tallow or coconut oil; sodium and ammonium alkyl ($C_9$–$C_{20}$) benzene sulfonates, particularly sodium linear secondary alkyl ($C_{10}$–$C_{15}$) benzene sulfonates; sodium alkyl glyceryl ether sulfates, especially those ethers of the higher alcohols derived from tallow coconut oil and synthetic alcohols derived from petroleum; sodium coconut oil fatty acid monoglyceride sulfates and sulfonates; sodium and ammonium salts of sulfuric acid esters of higher ($C_9$–$C_{18}$) fatty alcohol-alkylene oxide, particularly ethylene oxide reaction products; the reaction products of fatty acids such as coconut fatty acids esterified with isethionic acid and neutralized with sodium hydroxide; sodium and ammonium salts of fatty acid amides of methyl taurine; alkane monosulfonates such as those derived by reacting alpha-olefins ($C_8$–$C_{20}$) with sodium bisulfite and those derived by reacting paraffins with $SO_2$ and $Cl_2$ and then hydrolyzing with a base to produce a random sulfonate; sodium and ammonium $C_7$–$C_{12}$ dialkyl sulfosuccinates; and olefinic sulfonates, which term is used to describe the material made by reacting olefins, particularly $C_{10}$–$C_{20}$ alpha-olefins, with $SO_3$ and then neutralizing and hydrolyzing the reaction product. The preferred anionic detergent compounds are sodium ($C_{11}$–$C_{15}$) alkylbenzene sulfonates; sodium ($C_{16}$–$C_{18}$) alkyl sulfates and sodium ($C_{16}$–$C_{18}$)alkyl ether sulfates.

Examples of suitable nonionic surface-active compounds which may be used preferably together with the anionic surface-active compounds, include in particular, the reaction products of alkylene oxides, usually ethylene oxide, with alkyl ($C_6$–$C_{22}$) phenols, generally 2–25 EO, i.e. 2–25 units of ethylene oxide per molecule; the condensation products of aliphatic ($C_8$–$C_{18}$) primary or secondary linear or branched alcohols with ethylene oxide, generally 2–30 EO, and products made by condensation of ethylene oxide with the reaction products of propylene oxide and ethylene diamine. Other so-called nonionic surface-actives include alkyl polyglycosides, polyhydroxy fatty acid amides (e.g. $C_{12}$–$C_{18}$ N-methyl glucamide), long chain tertiary amine oxides, long chain tertiary phosphine oxides and dialkyl sulphoxides.

Amounts of amphoteric or zwitterionic surface-active compounds can also be used in the compositions of the invention but this is not normally desired owing to their relatively high cost. If any amphoteric or zwitterionic detergent compounds are used, it is generally in small amounts in compositions based on the much more commonly used synthetic anionic and nonionic actives.

Soaps may also be incorporated into the compositions of the invention, preferably at a level of less than 30% by weight. They are particularly useful at low levels in binary (soap/anionic) or ternary mixtures together with nonionic or mixed synthetic anionic and nonionic compounds. Soaps which are used are preferably the sodium, or less desirably potassium, salts of saturated or unsaturated $C_{10}$–$C_{24}$ fatty acids or mixtures thereof. The amount of such soaps can be varied between about 0.5 and about 25% by weight, with lower amounts of about 0.5 to about 5% being generally sufficient for lather control. Amounts of soap between about 2 and about 20%, especially between about 5 and about 15%, are used to give a beneficial effect on detergency. This is particularly valuable in compositions used in hard water when the soap acts as a supplementary builder.

The detergent compositions of the invention will normally also contain a detergency builder. Builder materials may be selected from (1) calcium sequestrant materials; (2) precipitating materials; (3) calcium ion-exchange materials; and (4) mixtures thereof.

In particular, the compositions of the invention may contain any one of the organic or inorganic builder materials, such as sodium or potassium tripolyphosphate, sodium or potassium pyrophosphate, sodium or potassium orthophosphate, sodium carbonate, the sodium salt of nitrilotriacetic acid, sodium citrate, carboxymethylmalonate, carboxymethyloxysuccinate, tartrate mono- and di-succinates, oxydisuccinate, crystalline or amorphous aluminosilicates and mixtures thereof.

Polycarboxylic homo- and copolymers may also be included as builders and to function as powder structurants or processing aids. Particularly preferred are polyacrylic acid (available under the trademark Acrysol from the Rohm and Haas Company) and acrylic-maleic acid copolymers (available under the trademark Sokalan from the BASF Corporation) and alkali metal or other salts thereof.

These builder materials may be present at a level of, for example, from 1 to 80% by weight, preferably from 10 to 60% by weight.

Upon dispersal in a wash water, the initial amount of peroxyacid should range in amount to yield anywhere from about 0.05 to about 250 ppm active oxygen per liter of water, preferably between about 1 to 50 ppm. The oxygen transfer agent should be present in the wash water from about 0.05 to about 100 ppm, preferably from 5 to 50 ppm per liter of water. Surfactant should be present in the wash water from about 0.05 to 1.0 grams per liter, preferably from 0.15 to 0.20 grams per liter. When present, the builder amount will range from about 0.1 to 3.0 grams per liter.

Apart from the components already mentioned, the detergent compositions of the invention can contain any of the conventional additives in the amounts in which such materials are normally employed in detergent compositions. Examples of these additives include lather boosters such as alkanolamides, particularly the monoethanolamides derived from palmkernel fatty acids and coconut fatty acids, lather depressants such as alkyl phosphates and silicones, antiredeposition agents such as sodium carboxymethylcellulose and alkyl or substituted alkylcellulose ethers, other stabilizers such as ethylene diamine tetraacetic acid, fabric softening agents, inorganic salts such as sodium sulfate and usually present in very small amounts, fluorescent whitening agents, perfumes, enzymes such as proteases, cellulases, lipases and amylases, germicides and colorants.

The oxygen transfer agents in combination with a peroxygen compound may be useful for removing stains both in consumer-type products and for industrial applications. Among consumer products incorporating this invention are laundry detergents, laundry bleaches, hard surface cleaners, toilet bowl cleaners, automatic dishwashing compositions and even denture cleaners. Stained consumer products benefiting from treatment with compositions of this invention may include clothes and other fabrics; household fixtures and appliances such as sinks, toilet bowls and oven ranges; tableware such as drinking glasses, dishes, cookware and utensils; and even dentures. Hair colorants may also be formulated with the bleach composition of this invention. the bleaching system of this invention may also be applied to industrial uses such as for the bleaching of wood pulp.

The system of the present invention may be delivered in a variety of product forms including powders, on sheets or other substrates, in pouches, in tablets, in aqueous liquids, or in nonaqueous liquids such as liquid nonionic detergents.

The following examples will more fully illustrate the embodiments of this invention. All parts, percentages and proportions referred to herein and in the appended claims are by weight unless otherwise illustrated.

EXAMPLE 1

Preparation of Mg Salt Intermediates of SULF-D

A. Preparation of Mg/Mg Salt Intermediate of SULF-D

Saccharin (7.32 g, 0.04 mole) and 30.0 mL anhydrous THF were charged into a 100 mL three-neck flask fitted with a mechanical stirrer, condenser, addition funnel and nitrogen flush system. The system was placed under nitrogen and the mixture was stirred and cooled in an ice-bath, and MeMgCl (28 mL 3.0M in THF, 2 equivalents) was then added dropwise in about 12 minutes. The ice-bath was then removed and the clear reaction solution stirred at room temperature for 24 hours, during which solids formed. The THF solvent was removed via distillation under slight vacuum to dryness to give a solid product further dried under vacuum. Colorless solids weighing 19.5 g were obtained. $^1$H-NMR (DMSO-D$_6$, 200 Mhz) of product showed the diMg salt intermediate to contain etherated THF to each Mg moiety. IR (Nujol) showed a strong absorbance at about 1650 cm$^{-1}$. The etherated THF on the DiMg salt intermediate was only partially removed by vacuum drying of the product at the refluxing temperature of xylenes (139°–142° C.) and 1,2-dichlorobenzene (180° C.).

B. Preparation of Na/Mg Salt Intermediate of SULF-D

The preparation of the Na/Mg salt intermediate of SULF-D was done in the same manner as "A" above except anhydrous Na-saccharin and one equivalent of MeMgCl were used. The reaction mixture remained heterogeneous throughout addition and stirring for 24 hours. Slightly colored solids weighing 13.8 g were obtained. $^1$H-NMR (DMSO-D$_6$, 200Mhz) of product showed the Na/Mg salt intermediate to contain only one etherated THF (to the Mg moiety). IR (Nujol) showed a strong absorbance at about 1640 cm$^{-1}$. The etherated THF on the Na/Mg salt intermediate was completely removed by vacuum drying at the refluxing temperature of xylenes (139°–142° C.).

EXAMPLE 2

Activation of Monopersulphate by Magnesium Sulfonimine Salts

Bleaching studies were conducted by comparing the performance of a common bleach (such as monopersulfate) with and without the presence of sulfonimine. In this regard, the stain removal observed without the intervention of sulfonimines served as an experimental blank and the amount of stain removal by the sulfonimine containing system constituted activation of a given bleach.

Stain bleaching experiments were conducted in a Terg-O-Tometer in 500 mL of milli-Q water using two tea-stained cotton cloths measuring 3×4 inches. OXONE ® was added to the system followed by an appropriate amount of sulfonimine salt. Washes were conducted at 32° C. In the pretreated run, the magnesium salts and SULF-D were pretreated in the wash liquor (no OXONE ®) for 15 minutes at 32° C. The ratio of KHSO$_5$ to catalyst was 10:1. Catalyst concentration for all runs was 6×10$^{-5}$ mole/liter.

Stain bleaching was measured reflectometrically using a Colorgard System/05 Reflectometer, Bleaching was indicated by an increase in reflectance, reported as $\Delta\Delta$R. In general a $\Delta\Delta$R of one unit is perceivable in a paired comparison while $\Delta\Delta$R of two units is perceivable monadically.

Results of activation using SULF-D with OXONE ® (ex DuPont, a trisalt of the following composition 2KHSO$_5$/KHSO$_4$/K$_2$SO$_4$) are reported in the following Table.

TABLE

| BLEACH AGENT | DIRECT ADDITION | | PRE-TREATED | |
|---|---|---|---|---|
| | $\Delta$R$_d$ | $\Delta\Delta$R$_d$ | $\Delta$R$_d$ | $\Delta\Delta$R$_d$ |
| OXONE only | 0.6 | — | 0.8 | — |
| SULF-D/OXONE | 4.4 | 3.8 | 4.4 | 3.6 |
| DiMg Salt/OXONE | 3.6 | 3.0 | 3.3 | 2.5 |
| Na/Mg Salt/OXONE | 3.5 | 2.9 | 3.7 | 2.9 |

Results listed in the Table indicate that the tea-stained cloths were bleached with salts of structure (1) almost as effectively as with SULF-D. Better results may even be obtainable through use of purified magnesium sulfonimine salts.

The foregoing description and Examples illustrate selected embodiments of the present invention. In light thereof, various modifications will be suggested to one skilled in the art, all of which are within the spirit and purview of this invention.

What is claimed is:

1. A method for bleaching a stained substrate, said method comprising contacting said stained substrate in an aqueous medium with a peroxygen compound present in an effective amount to clean said substrate and with an oxygen transfer agent present in an effective amount to catalyze activation of said peroxygen compound, whose structure is:

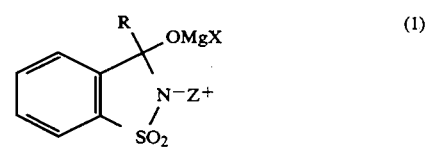

(1)

which is solvated with an ether or unsolvated, wherein:
R is a C$_1$–C$_{20}$ alkyl or aryl radical;
Z$^+$ is a metallic cation; and
X is a halide.

2. A method according to claim 1 wherein said substrate is selected from the group consisting of fabrics, household fixtures and tableware.

3. A method according to claim 1 wherein the oxygen transfer agent is present from about 0.05 ppm to about 100 ppm per liter of medium.

4. A method according to claim 1 wherein the peroxygen compound and oxygen transfer agent are present in a respective molar ratio ranging from about 250:1 to 1:2.

5. A method according to claim 4 wherein the ratio of peroxygen compound to oxygen transfer agent ranges from about 100:1 to 1:1.

6. A bleaching composition comprising:
(i) from about 1 to about 60% by weight of a peroxygen compound;
(ii) from about 0.05 to about 10% of an oxygen transfer agent whose structure is:

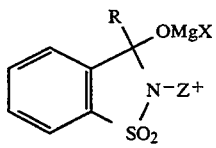 (1)

which is solvated with an ether or unsolvated, wherein:
R is a $C_1$–$C_{20}$ alkyl or aryl radical;
$Z^+$ is a metallic cation; and
X is a halide.

7. A composition according to claim 6 further comprising from about 1 to 80% of a detergent builder.

8. A composition according to claim 6 further comprising an effective amount for cleaning of an enzyme selected from the group consisting of proteases, cellulases, lipases, amylases and mixtures thereof.

9. A composition according to claim 6 wherein the peroxygen compound is present in an amount from about 1.5 to 25% and the oxygen transfer agent is present in an amount from about 0.2 to 5% by weight.

10. A composition according to claim 6 wherein the peroxygen compound is an inorganic material selected from the group consisting of perborate, percarbonate, perphosphate, persilicate and monopersulphate salts.

11. A composition according to claim 6 further comprising from about 0.5 to about 50% of a surfactant.

12. A composition according to claim 6 wherein R is methyl and $Z^+$ is selected from the group consisting of sodium and potassium cations.

13. A composition according to claim 6 wherein $Z^+$ is an alkalimetal cation.

14. A composition according to claim 6 wherein $Z^+$ is an alkalimetal cation.

15. A composition according to claim 6 wherein the peroxygen compound is an organic peroxyacid.

16. A composition according to claim 15 wherein the organic peroxyacid is selected from the group consisting of peracetic acid, monoperoxyphthalic acid and diperoxydodecanedioic acid.

17. A composition according to claim 16 wherein the monoperoxyphthalic acid is present as a magnesium hexahydrate salt.

18. A compound having the structure (1):

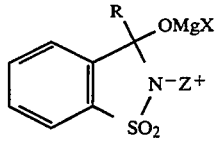 (1)

which is solvated with an ether or unsolvated, wherein:
R is a $C_1$–$C_{20}$ alkyl or aryl radical;
$Z^+$ is an alkalimetal cation; and
X is a halide.

19. A compound according to claim 18 wherein the alkalimetal cation is sodium.

20. A compound according to claim 18 wherein the alkalimetal cation is potassium.

* * * * *